United States Patent [19]

Reich et al.

[11] Patent Number: 6,090,995
[45] Date of Patent: *Jul. 18, 2000

[54] SURFACE MODIFYING COMPOSITION AND METHOD

[75] Inventors: Cary Reich, Laguna Hills; Jeffrey Forsberg, Irvine; Harold Levy, Seal Beach; Jean Toner-Webb, Irvine, all of Calif.

[73] Assignee: Surmodics, Inc., Eden Prairie, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/808,055

[22] Filed: Feb. 28, 1997

Related U.S. Application Data

[63] Continuation of application No. 08/650,026, May 17, 1996, abandoned, which is a continuation of application No. 08/469,619, Jun. 6, 1995, abandoned, which is a continuation of application No. 08/266,099, Jun. 27, 1994, abandoned, which is a continuation of application No. 07/955,245, Oct. 1, 1992, abandoned, which is a continuation of application No. 07/829,576, Feb. 3, 1992, abandoned, which is a continuation of application No. 07/700,034, May 7, 1991, abandoned, which is a continuation of application No. 07/408,059, Sep. 15, 1989, abandoned.

[51] Int. Cl.$^7$ ............................. A61F 2/02; B05D 3/06
[52] U.S. Cl. .......................................... 623/11; 427/2.24
[58] Field of Search ................ 623/4–6, 11; 351/160 R; 427/2, 2.24

[56] References Cited

U.S. PATENT DOCUMENTS

| | | |
|---|---|---|
| 2,714,721 | 8/1955 | Stone, Jr. . |
| 2,952,023 | 9/1960 | Rosen . |
| 3,438,374 | 4/1969 | Falb et al. . |
| 3,454,966 | 7/1969 | Rosen . |
| 3,826,678 | 7/1974 | Hoffman et al. . |
| 3,959,078 | 5/1976 | Guire . |
| 3,992,563 | 11/1976 | Tanaka . |
| 4,126,904 | 11/1978 | Shepard . |
| 4,189,546 | 2/1980 | Deichert et al. . |
| 4,223,984 | 9/1980 | Miyata et al. . |
| 4,240,163 | 12/1980 | Galin . |
| 4,346,482 | 8/1982 | Tennant et al. . |
| 4,452,235 | 6/1984 | Reynolds . |
| 4,589,881 | 5/1986 | Pierschbacher et al. . |
| 4,614,517 | 9/1986 | Ruoslahti et al. . |
| 4,624,669 | 11/1986 | Grendahl ..................... 623/5 |
| 4,652,459 | 3/1987 | Engelhardt ............... 427/2.24 |
| 4,656,083 | 4/1987 | Hoffman et al. . |
| 4,662,881 | 5/1987 | Nordan ....................... 623/5 |
| 4,676,790 | 6/1987 | Kern ........................... 623/5 |
| 4,704,131 | 11/1987 | Noishiki et al. . |
| 4,715,858 | 12/1987 | Lindstrom ................... 623/5 |
| 4,722,906 | 2/1988 | Guire . |
| 4,772,283 | 9/1988 | White ......................... 623/5 |
| 4,782,027 | 11/1988 | Lee et al. . |
| 4,799,931 | 1/1989 | Lindstrom ................... 623/5 |
| 4,828,563 | 5/1989 | Muller-Lierheim . |
| 4,839,464 | 6/1989 | McCarthy et al. ......... 530/326 |
| 4,919,659 | 4/1990 | Horbett et al. . |
| 4,973,493 | 11/1990 | Guire ........................... 427/2 |
| 4,979,959 | 12/1990 | Guire ......................... 623/66 |
| 4,983,181 | 1/1991 | Civerchia .................... 623/5 |
| 5,002,582 | 3/1991 | Guire et al. . |
| 5,028,597 | 7/1991 | Kodama et al. ........ 623/11 X |
| 5,080,924 | 1/1992 | Kamel et al. .............. 427/2 |
| 5,091,206 | 2/1992 | Wang et al. ................ 427/2 |
| 5,094,876 | 3/1992 | Goldberg et al. .......... 427/2 |
| 5,414,075 | 5/1995 | Swan et al. . |

FOREIGN PATENT DOCUMENTS

| | | |
|---|---|---|
| 195577 | 9/1986 | European Pat. Off. . |
| 290642 | 11/1988 | European Pat. Off. . |
| 2705234 | 8/1978 | Germany . |
| 3637260 | 5/1988 | Germany . |
| 60-197736 | 10/1985 | Japan . |
| 2-21755 | 11/1985 | Japan . |
| 544429 | 2/1977 | U.S.S.R. . |
| 700125 | 11/1979 | U.S.S.R. . |
| 8905616 | 12/1988 | WIPO . |
| 8904153 | 5/1989 | WIPO ......................... 623/11 |
| 8906945 | 8/1989 | WIPO . |
| 9000887 | 2/1990 | WIPO . |

OTHER PUBLICATIONS

Cazaux et al., "A Barium Selective Macrocyclic Tetralactam with Dimethyleneoxy Moieties", *Tetrahedron Letters* 30:1369–1372 (1989).

Yamamoto et al., "Restricted Internal Rotation of A t–Butyl Group Bonded to an Aromatic Ring", *Tetrahedron Letters* 27: 49–50 (1986).

Kroschwitz, "Plastics", pp. 462–464, in *Concise Encyclopedia of Polymer Science and Engineering*, ed., John Wiley and Sons, 1990.

Jentoft et al., "Labeling of Proteins by Reductive Methylataion Using Sodium Cyanoborohydride", *J. of Biol. Chem.* 254:4359–4365.

Jemmerson, "Antigenicity and native structure of globular proteins: Low frequency of peptide reactive antibodies", *Proc. Nat. Acad. Sci. USA*, 84:9180–9184 (Dec. 1987).

Stevens, "Considerations of the Interpretation of the Specificity of Monoclonal Antibodies Determined in Solid–Phase) Immunoassays", *Immunochemistry of Solid–Phase Immunoassay*, J.E. butler, ed., CRC Press, pp. 234–242 (1991).

Jemmerson, "Multiple Overlapping Epitopes in the three Antigenic Regions of Horse Cytochrome c", *J. Immunol*, 138:213–219 (Jan. 1, 1987).

Guire et al., Stepwise–Crosslinking Agents for Photocoupling of Enzymes and Lectins to Mannalian Cells, *Glycoconjugate Research*, vol. II, 1051 (1977).

*Primary Examiner*—David H. Willse
*Attorney, Agent, or Firm*—Fredrikson & Byron, P.A.

[57] ABSTRACT

Synthetic surfaces such as surfaces of implantable prosthetic devices are modified to enhance their ability to support the growth, migration and attachment of epithelial cells. A surface modifier composition is covalently bound to the synthetic surface, and an epithelial cell-supporting coating is applied to the modified surface. The surface modifier composition may also include an epithelial cell-supporting material. The invention is particularly suited towards the modification of synthetic epikeratophakia lenses.

15 Claims, No Drawings

SURFACE MODIFYING COMPOSITION AND METHOD

This application is a continuation of application Ser. No. 08/650,026, filed May 17, 1996, now abandoned, which is a continuation of Ser. No. 08/469,619, filed Jun. 6, 1995, now abandoned, which is a continuation of Ser. No. 08/266,099, filed Jun. 27, 1994, now abandoned, which is a continuation of Ser. No. 07/955,245, filed Oct. 1, 1992, now abandoned, which is a continuation of Ser. No. 07/829,576, filed Feb. 3, 1992, now abandoned, which is a continuation of Ser. No. 07/700,034, filed May 7, 1991, now abandoned, which is a continuation of Ser. No. 07/408,059, filed Sep. 15, 1989, now abandoned.

BACKGROUND OF THE INVENTION

The present invention relates to methods for modifying synthetic surfaces to support the growth, migration and attachment of epithelial, endothelial and other cell types both in vitro and in vivo, as well as the modified surfaces themselves. More specifically, the invention relates to methods for modifying the tissue-contacting surfaces of synthetic, implantable prosthetic devices, especially contact lenses, to better support the growth, migration and attachment of epithelial cells. The invention also relates to the prosthetic devices themselves.

There are a number of prosthetic devices which necessarily or desirably can be implanted either completely or partially beneath epithelial tissues. It is to be understood that reference to "epithelial" tissues herein includes epidermal tissue as well as other epithelial tissues. Implantation beneath the epithelium may be done for purposes of fixation of the device relative to other tissues and/or for cosmetic purposes. Examples of implanted prostheses include dental prostheses such as artificial teeth and bridgework, hearing aids, dermal implants, vascular access devices, such as those associated with hyperalimentation, colostomy devices and prosthetic corneas. While the present invention will be described with reference to prosthetic corneas for subepithelial implantation, and with specific reference to an epikeratophakia lens, it will be readily understood that the invention is not so limited.

The permanent implantation in the eye of a synthetic epikeratophakia lens has major advantages over operations such as radial keratotomy to correct severe vision problems. Implanting the synthetic epikeratophakia lens does not involve compromising the anterior chamber, for example. In the implantation procedure, the epithelial layer is removed via a trephine and scrape, the wound is undermined and the lens is tucked into place. Reepithelialization of the lens is expected to result in a permanent correction of vision for the patient. By "reepithelialization" it is meant not only the growth and migration (or 'spreading') of epithelial cells, but also the attachment and stabilization of these cells.

Reepithelialization of the implant is important for a variety of reasons. For example, reepithelialization is very important in order to ensure long term anchorage of an implant. The layer of new cells also acts as a barrier to prevent tear-born and other materials from depositing on the lens surface. Unfortunately, many materials which exhibit beneficial properties when formed into prosthetic devices (such as stability and lack of immune response) do not adequately support the growth, migration and attachment of epithelial cells.

It should be noted at the outset that the methods and modified synthetic surfaces of the present invention also are useful for the in vitro growth of epithelial cells. Epithelial cells grown in the laboratory upon surfaces modified according to the present invention exhibit growth, migration and attachment quite similar to the in vivo growth pattern of epithelial cells.

Thus, there is a need for a procedure whereby tissue-contacting surfaces of prosthetic devices or implants are modified in order to better support the growth, migration and attachment of epithelial cells. There is also a need for a procedure whereby surfaces of tissue culture plates and other laboratory equipment are modified to better support epithelial cells.

SUMMARY OF THE INVENTION

In one aspect, the present invention relates to a method for modifying a synthetic surface, comprising applying to a synthetic surface a surface modifying composition comprising a polymer having pendant functional groups capable of being converted to nitrene (or other highly reactive) groups and then converting the functional groups to highly reactive groups and thereby covalently binding the surface modifying composition to the synthetic surface. The "synthetic surface" may be a surface on a prosthetic device to be implanted into the body, or a surface of a tissue culture plate or similar device for supporting in vitro epithelial cell growth. The surface modifying composition optionally includes a material which supports or enhances the growth, migration and attachment of epithelial cells.

In another aspect, the present invention relates to a method for coating a synthetic surface with an epithelial cell-supporting coating, comprising applying to a synthetic surface a surface modifying composition comprising a polymer having pendant functional groups capable of being converted to nitrene (or other highly reactive) groups, converting the functional groups to highly reactive groups and thereby covalently binding the surface modifying composition to the polymeric surface to thereby modify the synthetic surface, and subsequently applying an epithelial cell-supporting coating onto the modified synthetic surface. Again, the "synthetic surface" may be a surface on a prosthetic device to be implanted into the body, or a surface of a tissue culture plate or similar device for supporting in vitro epithelial cell growth. In a preferred embodiment, the epithelial cell supporting coating is covalently coupled to the modified surface and is provided as a plurality of layers to more closely resemble native tissues. The coating also may be crosslinked so that it is stabilized and resistant to the action of collagenases and/or other proteases.

The present invention also relates to the modified synthetic surfaces per se. Thus, one aspect of the invention relates to a modified synthetic surface for supporting the growth, migration and attachment of epithelial cells, comprising a synthetic surface and a surface modifying composition covalently bound to the synthetic surface, wherein the surface modifying composition is capable of supporting epithelial cells.

In another aspect the invention provides a modified synthetic surface for supporting the growth and migration of epithelial cells, comprising a synthetic surface, a surface modifying composition covalently bound to the synthetic surface, and an epithelial cell-supporting coating disposed on the modified surface.

In one embodiment, the present invention provides a treated prosthetic device for subepithelial implantation in a human or animal comprising a prosthetic device having a surface modifying composition covalently bound thereto, and an epithelial cell supporting coating thereon.

In a particularly preferred embodiment, the invention provides a treated epikeratophakia lens comprising a synthetic lens, a surface modifying composition covalently bound to the lens, the surface modifying composition comprising a lysine polymer modified to contain pendant groups derived from N-hydroxy-succinimidyl-4-azidobenzoate or methyl 1-4-azidobenzoimidate, and an epithelial cell-supporting coating bound to the surface modifying composition and disposed on an exposed surface of the thus-treated lens. The epithelial cell-supporting coating preferably is covalently bound to the surface modifying composition. The epithelial cell-supporting coating also may be crosslinked in situ.

DETAILED DESCRIPTION

According to the present invention, a synthetic surface which ordinarily is not well suited to the binding of proteins is rendered more suitable for protein binding by the application of a surface modifier composition. This aspect of the invention is applicable to a wide variety of synthetic surfaces. This specification describes the invention in connection with hydrogels of, e.g., N-vinylpyrrolidone/methyl methacrylate copolymers commonly employed in contact lenses, but the invention is not so limited. Other hydrogels which may be modified according to the present invention include polymers of 2-hydroxyethylacrylate (e.g. polymacon), various copolymers of 2-hydroxyethylmethacrylate (e.g. hafilcon A and B, vifilcon A, tetrafilcon, dimefilcon, bufilcon, perfilcon, etc.), copolymers of N-vinylpyrrolidone (e.g. lidofilcon A and B, scafilcon A, surfilcon, vifilcon, filcon YA, etc.) and hydrogels containing collagen, for example as described in U.S. Pat. Nos. 4,452,925 and 4,388,428 and in P.N.A.S., USA, 77 (No. 4), 2064–2068 (1980).

The invention is also useful for providing modified surfaces on vascular graft implants. Such implants are fabricated, for example, from Dacron, polyurethanes, polypropylene, silicone, crosslinked collagens, collagen-plastic composites or phospho-lipid polymers.

Hydrogels are preferred constituents of epikeratophakia lenses due to their permeability and, consequently, their ability to transport oxygen, glucose and other nutrients and metabolites. Tissue culture plates manufactured from various polymers, such as polystyrene, are other synthetic surfaces which are enhanced by the methods of the present invention.

The surface modifier composition can be based on virtually any polymer having a plurality of pendant groups. Preferred polymers include a plurality of pendant amino and/or carboxyl groups and are exemplified by poly(amino acid)s such as poly(lysine). Other polyamines can be used, e.g. polyethyleneimine, as can other compounds with high amine content. In the alternative, polymers with high carboxyl or hydroxyl content may be used.

The molecular weight or chain length of the polymer employed in the surface modifier composition is not critical to the invention. For example, poly-L- and poly-D-lysines of 90,000 to 490,000 daltons have been used successfully in the surface modification method of the invention. Those skilled in the art will realize that polymers of lower (or higher) molecular weight also are useful.

In order to provide a highly stable modified surface, the surface modifier composition advantageously is covalently bound to the synthetic surface. Covalent binding of the surface modifier to the synthetic surface is accomplished via the use of appropriate coupling agents. In general, in surface modifier compositions based on polymers having a plurality of pendant groups, the pendant groups first are converted into functional groups capable of forming highly reactive radicals. The polymers then are covalently bound to the synthetic surface by converting the groups to their corresponding highly reactive functional groups, preferably via photolysis. The highly reactive functional groups then covalently couple with the synthetic surface.

Advantageously, the synthetic surface does not have to be derivatized or otherwise specially treated prior to the application of the surface modifier composition.

One preferred binding method is to covalently couple to the synthetic surface a surface modifier composition based on a poly(lysine) which has been modified so that about 10 mol percent of the pendant amino groups have a functional group containing a moiety capable of being converted into a nitrene or other highly reactive group. Nitrene groups are highly reactive with the synthetic surface and are formed, for example, by the photolysis of an azido ($—N_3$) group.

A portion of the pendant amino groups of a poly(lysine) polymer can be derivatized by reacting the lysine polymer with N-hydroxysuccinimidyl-4-azidobenzoate ("HSAB"), a polyfunctional compound which contains an amine-reactive group as well as an azido group. Upon incubation of a hydrogel lens with the HSAB-derivatized poly(lysine), and photolysis with UV light (typically in the 265–275 nm range), the poly(lysine) chains are covalently bound to the surface of the lens. Crosslinking among polymer chains (or with other materials which may be incorporated within the surface modifier composition as described hereinafter) also occurs. Methyl 1-4-azidobenzoimidate (MABI) is another compound useful for modifying the lysine polymer. Those skilled in the art will be able to select other appropriate coupling agents, with those that are activatable by U.V. or visible light being preferred.

Pre-treatment of the surface of some hydrogels with a methyl alcohol solution (which causes a swelling of the copolymer) can enhance binding.

The present invention also provides for the inclusion of a variety of other materials in the surface modifier compositions. If desired, the compositions can contain medicaments and/or other materials which promote wound healing. For example, an antibiotic material can be dispersed in the surface modifying composition. Suitable antibiotics include gentamicin, neomycin, bacitracin and the like. In addition, other antimicrobial agents, antiviral agents, anti-inflammatory agents, anti-protease agents, hormones, vitamins, analgesics, chelating agents, mitogenic agents (including growth factors) and the like may be incorporated in the surface modifying composition.

Preferred materials for incorporation into the surface modifier compositions are biological materials which are known to support the growth, migration and attachment of epithelial cells. These materials are referred to as "epithelial cell-supporting" materials herein. Advantageously, materials to be incorporated within the surface modifying compositions do not need to be modified or derivatized. Useful native, underivatized materials include (but are not limited to) collagen types I, III, IV and/or others, fibronectin, laminin, other basement membrane components or cell matrix components such as entactin, nidogen, heparin, heparin sulfate proteoglycan and virtually any other protein or other desired material (such as chondroitin sulfate) desired to be covalently attached to the synthetic surface. If desired, these materials may be altered, derivatized or crosslinked prior to being combined with the HSAB-modified poly (lysine) (or other surface modifier) and applied to the hydrogel. Upon photolysis, the included material is crosslinked by some of the nitrene groups attached to the poly(lysine), whereas other nitrene groups attached to the poly(lysine) covalently bind to the lens surface. Thus the lens (or other synthetic surface) is now coated with a covalently-attached layer of a surface modifier composition.

The invention also encompasses the provision of an epithelial cell-supporting coating over a surface which has been modified as described above. Such a coating can be based on virtually any epithelial cell-supporting material, although collagen (including combinations of types I, III and IV) presently is preferred. Combinations of epithelial cell-supporting materials are employed in certain preferred embodiments, including collagen with fibronectin, laminin and/or chondroitin sulfate incorporated therein.

Epithelial cell-supporting coatings containing materials which include a plurality of pendant groups can be covalently coupled to the modified surface via chemical crosslinking with a carbodiimide, dimethylpyrimidate, dimethylsuberimidate or another suitable compound. The epithelial cell-supporting coating itself can be crosslinked in situ by e.g. glutaraldehyde optionally followed by sodium cyanoborohydride. This final crosslinking step renders the coating less susceptible to collagenase and other proteases.

A derivatized poly(lysine) molecule is prepared by incubation of the native poly(lysine) with the bifunctional crosslinker HSAB under appropriate conditions. Any unreacted crosslinker is removed by ultrafiltration or other non-destructive methods such as dialysis. In addition to poly(lysine), other polymers capable of binding to a bifunctional crosslinker containing a secondary group capable of forming a highly-reactive radical upon exposure to light may be used in this process.

The following examples are intended to illustrate the practice of the invention and are not intended to limit its scope in any way.

EXAMPLE I

An HSAB-derivatized poly(lysine) is prepared according to the procedure described in detail in Example V. HSAB is available from Pierce Chemical Company, Rockford, Ill., USA. A hydrogel lens prepared from an N-vinylpyrrolidone, methyl methacrylate copolymer is placed in a chamber anterior side up and incubated with the HSAB-derivatized poly(lysine) solution (2.0 to 10.0 mg/ml, preferably 5.0 mg/ml) (which is hereinafter referred to as "HSAB-plys"), with or without 10–20% MeOH added to swell the hydrogel during coating. The lens is then irradiated with UV light for 4 to 10 minutes per coat for 5 to 10 coats. The lens is then extracted in aqueous solutions of plain water, saline or 0.05 M glacial acetic acid to remove unbound HSAB-plys.

The coating is visualized on a test lens from the lot by a novel Coomassie™ staining/destaining process that visualizes only covalently bound HSAB-plys on the hydrogel lens. The coated lens and a control (uncoated) lens are submerged in a stain composed of 0.1 to 0.25% (w/v) Coomassie Brilliant Blue R (Sigma B-0630), 7 to 10% glacial acetic acid and 25% methanol in water (see Laemmli, U.K., Nature 227, 680 (1970). Alternately, a stain composed of 0.1 to 0.25% (w/v) Coomassie Brilliant Blue R, 0 to 10% glacial acetic acid, 45% methanol and 45% acetone (balance water, methanol and/or acetone) may be used. While the Laemmli process employs acetic acid to fix the protein(s) of interest to an acrylamide gel, the use of acetic acid is not required in this process as the poly(lysine) is covalently bound to the synthetic surface.

The lenses are incubated in the stain for 20 to 30 minutes. The lenses are extracted with three 20-minute extractions (or until the control lens is completely clear) of destaining solution composed of 0 to 10% (w/v) glacial acetic acid, 45% methanol and 45% acetone (balance water, methanol and/or acetic acid) to remove the unbound Coomassie stain. The acetone advantageously swells the hydrogel to aid the release of unbound stain. Under these staining/destaining conditions unbound HSAB-plys (or plys alone) is removed from the lens and only lenses to which the poly(lysine) is covalently bound retain the stain.

These lenses, having surfaces modified with HSAB-plys alone, are capable of binding epithelial cells, but the cells do not seem to spread well. Thus it is desirable to bind collagen or other epithelial cell-supporting materials to this poly (lysine) in order to support epithelial growth. This may be done in one step, by incorporating an epithelial cell-supporting material within the surface modifier composition, or in several steps, by providing an epithelial cell-supporting coating over the surface modifier composition.

Variations in the destaining solution mentioned above are possible. In general, destaining solutions containing 10–45% acetone, 25–45% methanol, 10–25% glyme (dimethoxyethane), balance water and/or glacial acetic acid (HOAc) are useful for removing unbound Coomassie-type stain while swelling the hydrogel (or other polymer). Specific examples are set forth below wherein all amounts are percent (w/v):

|  | Acetone | MeOH | $H_2O$ | HOAc | Glyme |
| --- | --- | --- | --- | --- | --- |
| 1) | 45 | 45 | 0–10 | 0–10 |  |
| 2) | 10 | 45 | 35 | — | 10 |
| 3) | 25 | — | 50 | — | 25 |
| 4) | 10 | 25 | 55 | — | 10 |

The acetone component of the destaining solution appears to function as a solvent which softens the poly(methyl methacrylate) component of the hydrogel to aid in the release of unbound stain. Other solvents which function in a similar manner may be employed in lieu of or in combination with acetone. Of course, the choice of particular solvents will be based on the composition of the synthetic surface to be treated in accordance with the invention.

EXAMPLE II

In a one step method, HSAB-plys and unmodified collagen may be simultaneously covalently bound to the hydrogel surface in the following manner. A hydrogel lens is incubated with a solution containing both HSAB-plys and combinations of collagen I, III and IV (optionally along with fibronectin, laminin, chondroitin sulfate or any other desired material) in a range from 100:1 to 1:100 ratio by weight HSAB-plys:collagen (or other ratios allowing some of the HSAB moieties on the poly(lysine) to be used for coupling to the hydrogel lens, and some to be used for coupling to the collagen). Multiple coats (5–10) are coupled via irradiation onto the lens. The protein coating may be visualized by staining as described above. Alternate specific stains may be used to distinguish collagen or other materials from the poly(lysine) staining; however, Coomassie stain can also distinguish the collagen/poly(lysine) coating from a poly (lysine) coating using the procedure described in Example I. As further evidence of the covalent binding of collagen and poly(lysine) to the hydrogel surfaces, autoclaving these coated lenses results in retention of the collagen/poly(lysine) coating as visualized by the staining procedure. However, cell culture results on such autoclaved lenses are negative, i.e. cells do not adhere or spread on these lenses. Thus, even when the collagen is denatured by autoclaving, it is still covalently bound to the hydrogel surface.

EXAMPLE III

In a two step method, HSAB-plys and collagen (or other molecules) may be bound to the surface of the hydrogel. First, HSAB-plys is covalently bound to the surface by incubation with the hydrogel in the presence of UV light, as discussed above. Secondly, collagen, and/or other molecules containing carboxyl groups are incubated with the poly (lysine) coated lens in the presence of a crosslinker such as 1-ethyl-3-(3-dimethylaminopropyl) carbodiimide ("EDC", available from Pierce Chemical Company, Rockford, Ill., USA), or other carbodiimides, which crosslinks the collagen to the bound poly(lysine), and thus to the hydrogel lens. If other derivatized polymers are used, instead of poly(lysine), and covalently bound to the hydrogel surface, then other crosslinkers are chosen which can crosslink functional groups on the polymer to materials which will support epithelial growth, or other molecules as desired. Thus both homobifunctional and heterobifunctional crosslinkers may be used where appropriate. Multiple coats (4–5) are covalently bound to the surface in this fashion. Extensive extraction with saline or a solution of 100 to 500 $\mu$g/ml gentamicin sulfate in saline is performed to remove any non-covalently bound materials and reagents.

The EDC crosslinking may be done at a low pH, as is standard, or at physiological pH using N-hydroxysulfosuccinimide ("Sulfo-NHS" also available from Pierce Chemical Company) as a co-reactant in order to gently couple sensitive molecules or materials, such as laminin or basement membrane extract, which may be desired in the coating. Laminin may be added during the neutral pH EDC crosslinking. After an incubation of the lens with the EDC/collagen/low pH mixture, the pH may be raised before the addition of laminin or other sensitive molecules to be bound.

The above lenses, covalently coated with poly(lysine) and collagen (and/or other epithelial cell-supporting materials) may be further crosslinked with glutaraldehyde alone, or glutaraldehyde followed by sodium cyanoborohydride, to stabilize the lenses to collagenase activity and to provide a more desirable coating for epithelial migration. The coated lenses may be crosslinked with a low concentration glutaraldehyde solution (0.2%), and/or with a high concentration solution (up to 2.0%), or other concentrations, in a sodium phosphate/sodium chloride buffer. The lenses are extensively extracted and then treated with a borate/glycine buffer to neutralize any unreacted glutaraldehyde. The unbound materials are removed by extensive extraction in aqueous solutions of saline or gentamicin sulfate in saline as described above. The stability of the coating to collagenase digestion on such lenses is greater than that of control lenses without glutaraldehyde crosslinking, as visualized by the stain/destaining method. In cell culture and in animal studies (rabbits and cats) these lenses perform well, indicating that post or intermediate crosslinking with concentrations ranging from 0.2% to 2.0% glutaraldehyde does not deter epithelial cell growth, and may in fact enhance the growth of epithelial cells. The further treatment of these lenses with sodium cyanoborohydride to further stabilize the crosslinks formed by the glutaraldehyde (to prevent possible reversal with time) also does not interfere with epithelial cell growth.

Additionally, the above lenses which have poly(lysine) surface modifier and collagen layers (and optionally also include fibronectin, laminin, or other desired materials), followed by glutaraldehyde treatment, may now have additional coats of collagen I, III and/or IV, laminin, fibronectin, or any combination of these or other appropriate molecules to support epithelial growth, bound to the lens by the methods described above. The additional coats will present a more native surface to the spreading epithelial cells. If desired, these extra coats may also be followed by a crosslinking step (with glutaraldehyde for example) which further crosslinks all coats. Hydrogel lenses treated as above have given 100% cell confluence in 1–2 days in cell culture. When implanted in rabbits, the lenses are essentially completely reepithelialized in 4–7 days.

The following examples are intended to illustrate further the practice of the invention and are not intended to limit its scope in any way.

EXAMPLE IV

Coupling Collagen Directly to a Hydrogel Surface Which Contains Carboxyl Groups

The hydrogel in this Example is a polymer consisting of vinyl pyrrolidone and methyl methacrylate, containing methacrylic acid as a source of carboxyl functional groups. Collagen is type I, calf skin, 2.5 mg/ml as supplied in acidic solutions. The hydrogel was incubated with collagen and EDC for 1 hr. at room temperature in a pH 4 sodium phosphate buffer, and subsequently rinsed. As visualized by protein staining, the hydrogel acquired a thin protein coating.

EXAMPLE V

Preparation of Poly-L-lysine Derivatized with a Heterobifunctional Crosslinking Reagent, HSAB Poly-L-lysine (490,000 daltons), 500 mg, is dissolved into 95 ml of 0.5 M triethanolamine, 0.2 M NaCl buffer, pH 8.3–8.4. A 10% molar ratio of HSAB to total available amino groups is dissolved in a small volume of DMF (3 ml) in the dark. The HSAB in DMF is then added, while stirring, to the poly-L-lysine and incubated at 4° C. in the dark for 2 hours, or until the process of binding is complete as determined by HPLC using a size exclusion column. The HSAB-derivatized poly-L-lysine (HSAB-plys) is exchanged into water via ultrafiltration for several changes, is sterile filtered and stored in the dark at 4° C. until use.

EXAMPLE VI

Coupling HSAB-poly-L-lysine to a Non-functionalized Hydrogel Surface by Exposure to UV Light The hydrogel (vinyl pyrrolidone, methylmethacrylate copolymer with no carboxyl or amine functional groups) lenses are incubated with a 5 mg/ml solution of HSAB-plys (from example V) and photolyzed with UV light for 10 minutes. The solution is exchanged, and the process repeated for a total of 10 times to obtain 10 coats of poly-L-lysine covalently bound to the lens surface and to itself.

The lenses are rinsed extensively and put into cell culture, or implanted into rabbits. Cell culture results show isolated patches of cells which show up to 40% attachment to the surface by day 2–5. These results imply that although cell attachment may be achieved, cell spreading is not achieved on this surface. Rabbit implants were stable, but epithelialization of the lens surface did not occur.

EXAMPLE VII

Coupling HSAB-poly-L-lysine and Collagen Simultaneously to a Non-functionalized Hydrogel Surface by Exposure to UV Light Hydrogel lenses were incubated with solutions containing molar ratios of 10:1, 30:1, and 100:1 collagen IV:HSAB-plys, with collagen concentration of 2 mg/ml. Ten coats were applied using 10 minute exposures to UV light. Lenses with such coatings support epithelial growth in cell culture, with 85–90% coverage by day 1, and 100% by day 4. Rabbit implants show epithelial growth up to the trephine cut by day 2, and at best, epithelial coverage up to 35% by day 6, followed by complete retreat of the epithelium from the lens by day 8.

EXAMPLE VIII

Crosslinking of Coated Hydrogel Lenses with Glutaraldehyde

Lenses were coated with UV light as in example VII with 15:1 collagen IV to HSAB-plys. The coated lenses were then incubated for two 45 minute treatments with solutions of 0.2% glutaraldehyde in a 0.5 M sodium phosphate, 0.15 M sodium chloride, pH 7.4 buffer. Lenses were rinsed with water for injection and incubated with a 0.05 M sodium borate, 0.025 M glycine solution for three incubations of 20 minutes each, followed by extensive rinsing in aqueous solutions. These lenses support epithelial growth in cell culture, with 90% coverage by day 1, and 100% by day 2. Rabbit implants show a maximum coverage of the lenses of 40% by day 3 to day 8, followed by regression to 0% by day 14. A cat implant showed a stable maximum coverage of 70% after 5 weeks, followed by a 3 day regression to 50% and extrusion.

EXAMPLE IX

Addition of 1% Chondroitin Sulfate to the Coating of Hydroqel Lenses

Lenses were coated using UV light, similarly to example VII, with 10 coats for 5 minutes UV each and a 15:1 cell-supporting material:HSAB-plys solution, with the cell-supporting material consisting of a solution of 2.0 mg/ml collagen and a 0.02 mg/ml chondroitin sulfate. Lenses were treated with glutaraldehyde as in Example VIII. Rabbit implant results are similar to those of Example VIII with a maximum of 40% coverage by day 4, and regression to 20% by day 9.

Example X

Addition of Collagen Coats via Carbodiimide Coupling to the Collagen:poly-lysine Coated Lenses Lenses were prepared similarly to those in example VII using collagen IV:HSAB-plys in a 15:1 molar ratio, for 9–10 coats. These lenses were then incubated with 2.0 mg/ml collagen IV and 19.2 mg/ml EDC under acidic conditions for 4 coats of 20 minutes each. Lenses had either no further additions, or had additions of 1% by weight of chondroitin sulfate (CS), fibronectin (Fn), or chondroitin sulfate and fibronectin. The lenses were treated with glutaraldehyde as in example VIII. Results for lenses with the following EDC coats are seen in Table I. The expressed percentages refer to reepithelialization.

TABLE I

| | |
|---|---|
| Col IV: | Cell culture, 80% by day 2, 90% by day 6, healthy cells. |
| | Rabbit implant, 85% by day 7, 100% by day 8 through 9, with regression to 10% by day 14. |
| Col IV + 1% CS: | Cell culture, 80% by day 2, healthy cells. |
| Col IV + 1% Fn: | Rabbit implant, 100% by day 4, 90% by day 8, with regression to 10% by day 14. |
| Col IV + 1% Fn + 1% Cs: | Cell culture, 80% by day 2, 95–98% by day 6 with some rounded cells. |
| | Cat implant, 100% epithelial coverage, stable out to 30 weeks at last observation |

EXAMPLE XI

Addition of HSAB-plys with UV, Neutral pH EDC Coating, Laminin, 2.0% Glutaraldehyde Crosslinking, and Extra EDC Overcoats of Collagen IV, Chondroitin Sulfate and Laminin to Lenses Coated as in Example VIII, with Various Other Treatments as Indicated Below (Types 1–7)

All lenses were coated in the following manner (steps 1–7):
1. 5 HSAB-poly-L-lysine UV coats with 10% MeOH, irradiated for 4 minutes each.
2. 10 coats Col I:HSAB-poly-L-lysine, 12:1 ratio by weight, at 1 mg/ml collagen and irradiated as in step 1.
3. 4 coats EDC/NHS-sulfo* pH 7.4 with collagen IV at 2 mg/ml and laminin**.
4. 0.2% glutaraldehyde overnight under the conditions in example VIII.
5. 2.0% glutaraldehyde for 45 minutes under the same conditions.
6. 2 coats EDC/NHS-sulfo pH 7.4 with collagen IV, laminin, and 0.2% chondroitin sulfate.
7. One of the following differences or additions to the treatment:

Type 1: No further treatment.

Type 2: Poly-D-lysine was used in steps 1 and 2.

Type 3: EDC/NHS-sulfo coats of underivatized poly-lysine were added in between the first three coats of step 3.

Type 4: A 2.0% glutaraldehyde crosslinking step after all coats (after step 6 above) under the same conditions as in Example VIII.

Type 5: A 2.0% glutaraldehyde step as in Type 4 followed by sodium cyanoborohydride treatment.***

Type 6: Sodium cyanoborohydride treatment alone after all coats (after step 6 above).

Type 7: Lenses were etched before coating to give a rough coating surface.

\* EDC/NHS-sulfo was 19.2 mg/ml EDC, 9.6 mg/ml NHS-sulfo at neutral pH in sodium phosphate buffer.

\*\* Laminin was provided by adding 13 μg/ml laminin to the collagen mixture.

\*\*\* Sodium cyanoborohydride was provided by adding 50 mM sodium cyanoborohydride in 0.5 M sodium acetate, pH 4.4.

The results obtained are as follows:

Types 1 through 6 lenses were implanted in rabbits. The best lens from Type 5 achieved 98% coverage by day 8 and maintained 75% coverage as of day 62. The best lens from Type 4 achieved 80 to 85% coverage by day 7 and maintained 70% coverage as of day 29. The best lens from Type 3 achieved 70 to 75% coverage by day 6 and maintained 60% coverage as of day 22. Lenses from Types 1, 2 and 6 achieved maximum epithelial cell coverage of around 70% and regressed to 15% or less by day 40.

Although the present invention has been described in connection with certain preferred embodiments and specific Examples, it is not so limited. Variations within the scope of the appended claims will be readily apparent to those skilled in the art.

We claim:

1. A method for modifying a synthetic surface, the method comprising the steps of:
   a) applying to the synthetic surface a surface modifying composition comprising (i) polymer molecules having pendant functional groups capable of being converted by photolysis to highly reactive groups, and (ii) molecules of another material lacking pendant functional groups capable of being converted by photolysis to highly reactive groups,
   b) photolysing the composition in order to convert the functional groups to highly reactive groups and thereby simultaneously covalently bind the polymer molecules by reaction of the highly reactive groups with the other material and the synthetic surface, wherein the surface is the surface of a device selected from the group consisting of a prosthetic device to be implanted into the body, a tissue culture plate, and a device for supporting in vitro epithelial cell growth.

2. A method according to claim 1 wherein the polymer molecules are selected from the group consisting of polymers comprising a plurality of pendant amino and/or carboxyl groups.

3. A method according to claim 2 wherein the polymer molecules are selected from the group consisting of poly (amino acid)s.

4. A method according to claim 1 wherein the other material supports the growth, migration and attachment of cells.

5. A method according to claim 1 wherein the other material is a biological material selected from the group consisting of antibiotics, antimicrobial agents, antiviral agents, anti-inflammatory agents, anti-protease agents, hormones, vitamins, analgesics, chelating agents, mitogenic agents.

6. A method according to claim 1 wherein the surface is fabricated from the group consisting of Dacron, polyurethanes, polypropylene, silicone, crosslinked collagens, collagen-plastic composites and phospho-lipid polymers.

7. A method according to claim 1 wherein the surface comprises a hydrogel.

8. A modified synthetic surface formed by a process that comprises the steps of a) providing a synthetic surface, b) applying to the synthetic surface a surface modifying composition comprising (i) polymer molecules having pendant functional groups capable of being converted by photolysis to highly reactive groups, and (ii) molecules of another material lacking pendant functional groups capable of being converted by photolysis to highly reactive groups, and c) photolysing the composition in order to convert the functional groups to highly reactive groups and thereby simultaneously covalently bind the polymer molecules by reaction of the highly reactive groups with the other material and the synthetic surface, wherein the surface is the surface of a device selected from the group consisting of the surface of a prosthetic device to be implanted into the body, the surface of a tissue culture plate, and the surface of a device for supporting in vitro epithelial cell growth.

9. A surface according to claim 8 wherein the polymer molecules are selected from the group consisting of polymers comprising a plurality of pendant amino and/or carboxyl groups.

10. A surface according to claim 9 wherein the polymer molecules are selected from the group consisting of poly (amino acid)s.

11. A surface according to claim 8 wherein the other material supports the growth, migration and attachment of cells.

12. A surface according to claim 8 wherein the other material is a biological material selected from the group consisting of antibiotics, antimicrobial agents, antiviral agents, anti-inflammatory agents, anti-protease agents, hormones, vitamins, analgesics, chelating agents, mitogenic agents.

13. A surface according to claim 8 wherein the surface is fabricated from the group consisting of Dacron, polyurethanes, polypropylene, silicone, crosslinked collagens, collagen-plastic composites and phospho-lipid polymers.

14. A surface according to claim 8 wherein the surface comprises a hydrogel.

15. A prosthetic device comprising a modified synthetic surface according to claim 8.

* * * * *